US012653294B2

(12) United States Patent
Croix

(10) Patent No.: US 12,653,294 B2
(45) Date of Patent: Jun. 16, 2026

(54) DEVICE FOR SEPARATELY DISPENSING MATERIALS FOR USE TOGETHER ON HUMAN SKIN

(71) Applicant: SunFly Brands, Inc., Seattle, WA (US)

(72) Inventor: Michael Croix, Seattle, WA (US)

(73) Assignee: SunFly Brands, Inc., Seattle, WA (US)

( * ) Notice: Subject to any disclaimer, the term of this patent is extended or adjusted under 35 U.S.C. 154(b) by 1205 days.

(21) Appl. No.: 16/095,867

(22) PCT Filed: May 18, 2017

(86) PCT No.: PCT/US2017/033312
§ 371 (c)(1),
(2) Date: Oct. 23, 2018

(87) PCT Pub. No.: WO2017/201274
PCT Pub. Date: Nov. 23, 2017

(65) Prior Publication Data
US 2019/0166976 A1 Jun. 6, 2019

Related U.S. Application Data

(60) Provisional application No. 62/338,235, filed on May 18, 2016.

(51) Int. Cl.
*A45D 34/00* (2006.01)
*A45D 34/04* (2006.01)
(Continued)

(52) U.S. Cl.
CPC ............. *A45D 34/00* (2013.01); *A45D 34/04* (2013.01); *A45D 34/042* (2013.01); *A45D 34/06* (2013.01);
(Continued)

(58) Field of Classification Search
CPC ...... A45D 34/00; A45D 34/04; A45D 34/042; A45D 34/06; A45D 40/22; A45D 40/24;
(Continued)

(56) References Cited

U.S. PATENT DOCUMENTS 4,717,050 A 1/1988 Wright
5,662,245 A 9/1997 Grant
(Continued)

FOREIGN PATENT DOCUMENTS

EP 1819630 A2 * 8/2007 ........... B65D 43/161
FR 2598686 B1 2/1991
(Continued)

OTHER PUBLICATIONS

Merriam-Webster website definition, Stamp, 2023, Merriam Webster, https://www.merriam-webster.com/dictionary/stamp (Year: 2023).*
(Continued)

*Primary Examiner* — Don M Anderson
*Assistant Examiner* — John Martin Hoppmann
(74) *Attorney, Agent, or Firm* — Schwabe, Williamson & Wyatt, P.C.

(57) ABSTRACT

Methods and devices are provided for containing and separately dispensing a sunscreen and a UV indicator for use with the sunscreen to indicate effectiveness thereof. A flexible tube or container defines a primary chamber containing sunscreen therein and has a double flip-top cap mounted thereon. The double flip-top cap comprises a base mounted to the flexible tube and via which the sunscreen is dispensed. A middle section of the cap is hinged to the base and provides access to the primary chamber. A top section of the cap is hinged to the middle section. The middle section and top section cooperate to define a secondary chamber containing the UV indicator, with the top section providing access to the secondary chamber. The secondary chamber
(Continued)

can contain a pre-inked stamp, or a stamp and ink pad impregnated with the UV indicator. The UV indicator is applied to one or more small regions of the skin under the sunscreen, and changes color to indicate effectiveness of the sunscreen.

13 Claims, 11 Drawing Sheets

(51) Int. Cl.

| | |
|---|---|
| *A45D 34/06* | (2006.01) |
| *A45D 40/22* | (2006.01) |
| *A45D 40/24* | (2006.01) |
| *A61K 8/04* | (2006.01) |
| *A61M 35/00* | (2006.01) |
| *A61Q 17/04* | (2006.01) |
| *B65D 51/18* | (2006.01) |
| *B65D 51/28* | (2006.01) |

(52) U.S. Cl.
CPC ............. *A45D 40/22* (2013.01); *A45D 40/24* (2013.01); *A61K 8/046* (2013.01); *A61M 35/003* (2013.01); *A61Q 17/04* (2013.01); *B65D 51/18* (2013.01); *B65D 51/28* (2013.01); *A45D 2200/055* (2013.01); *A45D 2200/057* (2013.01); *A45D 2200/25* (2013.01); *A61K 2800/45* (2013.01); *A61K 2800/884* (2013.01); *B65D 2251/0015* (2013.01); *B65D 2251/0021* (2013.01); *B65D 2251/0087* (2013.01)

(58) Field of Classification Search
CPC ........ A45D 2200/055; A45D 2200/057; A45D 2200/25; A45D 40/265; A45D 34/045; A45D 33/24; A45D 40/221; A61K 8/046; A61K 2800/45; A61K 2800/884; A61M 35/003; A61Q 17/04; B65D 51/18; B65D 51/28; B65D 2251/0015; B65D 2251/0021; B65D 2251/0087; B65D 83/00; B65D 25/04; B65D 81/3261; B65D 83/68; B65D 81/3205; B65D 21/0228; B65D 35/22; B65D 75/323; B65D 53/02; B65D 21/0209; B65D 5/66; B65D 2251/0078; B65D 43/161; B65D 51/24; G01J 1/429; G01J 1/50
USPC ........ 220/254.2, 254.1, 520, 4.26, 255, 810, 220/23.83, 521; 222/129, 143, 132, 138, 222/485, 556, 256, 93; 215/235, 230, 6; 40/311; 132/294, 314, 317
See application file for complete search history.

(56) References Cited

U.S. PATENT DOCUMENTS

| | | | | |
|---|---|---|---|---|
| 6,531,116 | B1 * | 3/2003 | Suares | ................... A61K 8/498 |
| | | | | 514/846 |
| 6,874,966 | B2 * | 4/2005 | Duqueroie | ........... A45D 40/265 |
| | | | | 132/294 |
| 7,845,871 | B2 | 12/2010 | Thiebaut | |
| 8,215,861 | B2 * | 7/2012 | Gueret | ................. A45D 40/262 |
| | | | | 401/266 |
| 9,658,101 | B1 | 5/2017 | Levine | |
| 10,457,451 | B2 * | 10/2019 | Hwang | ................ A45D 34/042 |
| 2002/0022008 | A1 * | 2/2002 | Forest | ........................ G01J 1/50 |
| | | | | 424/59 |
| 2002/0076256 | A1 * | 6/2002 | Gueret | ................. B65D 83/285 |
| | | | | 401/126 |
| 2002/0170915 | A1 * | 11/2002 | Hierzer | ................... B65D 51/28 |
| | | | | 220/521 |
| 2004/0052568 | A1 * | 3/2004 | Gueret | ................... B65D 47/42 |
| | | | | 401/118 |
| 2004/0190974 | A1 * | 9/2004 | Cantone | ............. A46B 11/0006 |
| | | | | 401/25 |
| 2005/0145525 | A1 | 7/2005 | Williams | |
| 2005/0284498 | A1 * | 12/2005 | Demarest | ............... B65D 51/28 |
| | | | | 132/289 |
| 2008/0146529 | A1 | 6/2008 | Hansenne et al. | |
| 2009/0127263 | A1 | 5/2009 | Hylton | |
| 2013/0200072 | A1 | 8/2013 | Wightman | |
| 2014/0332024 | A1 * | 11/2014 | Finney | ................... A45D 34/04 |
| | | | | 132/200 |
| 2016/0068313 | A1 * | 3/2016 | Hart | ..................... B65D 43/169 |
| | | | | 220/254.2 |
| 2016/0114942 | A1 | 4/2016 | Mussio | |
| 2017/0071536 | A1 | 3/2017 | Tibbits | |

FOREIGN PATENT DOCUMENTS

| | | | | | |
|---|---|---|---|---|---|
| JP | | 2001286329 | A | * | 10/2001 ........... A45D 29/007 |
| WO | | 2002003949 | | | 11/2003 |
| WO | | 2005/068308 | A1 | | 7/2008 |
| WO | | 2018232387 | A1 | | 12/2018 |
| WO | WO-2020092476 | | A1 | * | 5/2020 |

OTHER PUBLICATIONS

De Jong, Jaap J.D., et al. Photochromic Properties of Perhydro- and Perfluorodithienylcyclopentent Molecular Switches. Eur. J. Org. Chem, 2003, pp. 1887-1893.

International Preliminary Report on Patentability for PCT/US2017/033312, mailed on Nov. 29, 2018. 7 pages.

International Search Report and Written Opinion for PCT/US2017/033312, mailed on Aug. 10, 2017. 9 pages.

Sun Stamp: http://ifworlddesignguide.com/entry/142460-sun-stamp/ ; accessed on Feb. 25, 2019. 2 pages.

\* cited by examiner

FIG. 1

FIG. 2A
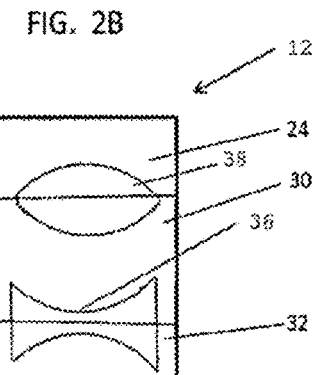
FIG. 2B
FIG. 2C
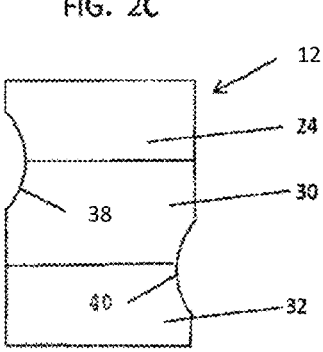
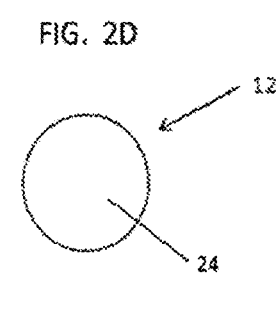
FIG. 2D

30

46

50

30

52

48

30

50

48

56     46

FIG. 4D
FIG. 4E
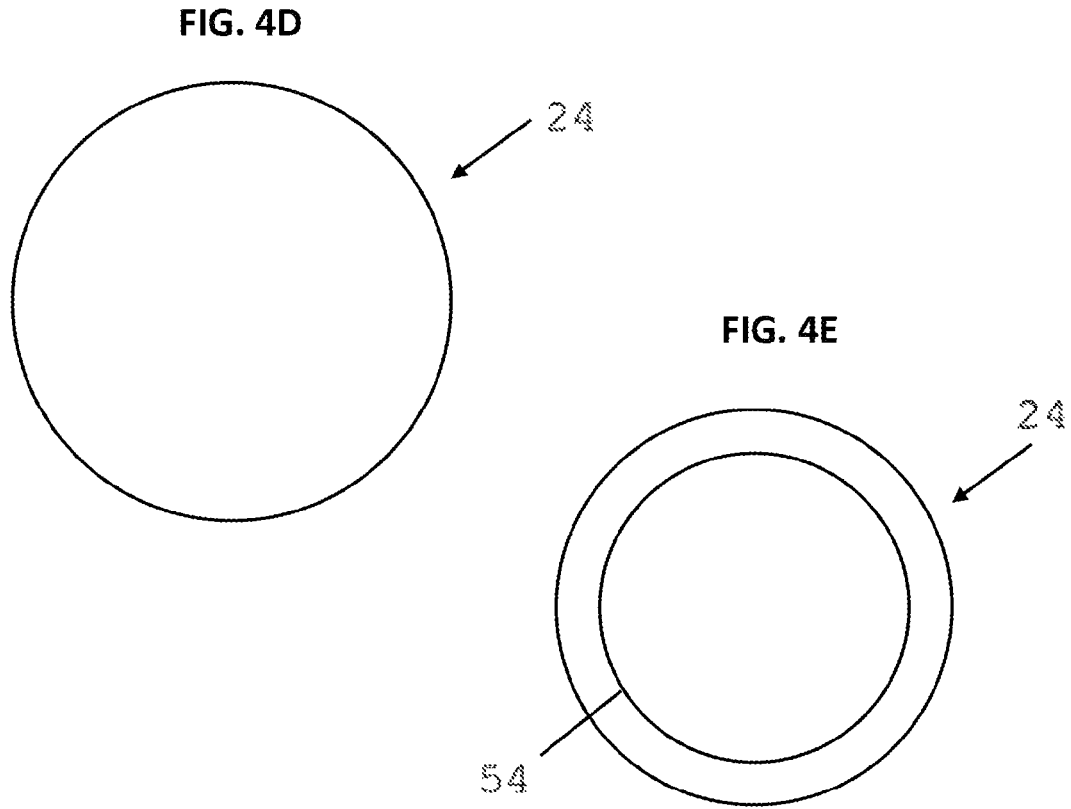
FIG. 4F
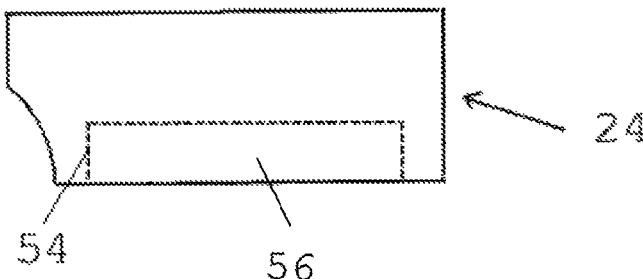

FIG. 5A
FIG. 5B
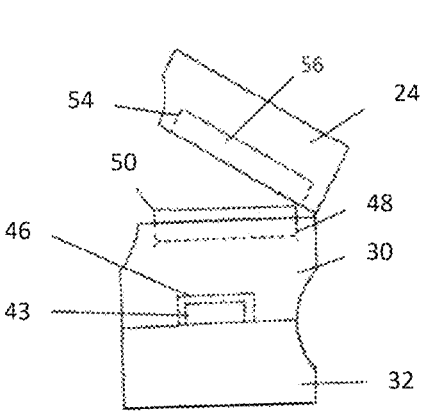
FIG. 5C
FIG. 5D
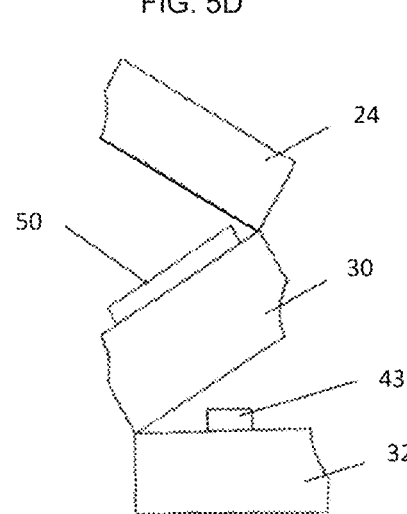

DEVICE FOR SEPARATELY DISPENSING MATERIALS FOR USE TOGETHER ON HUMAN SKIN

BACKGROUND

Technical Field

The present disclosure relates generally to methods and devices for containing and separately dispensing materials for use together on human skin. In particular it relates to methods and devices for containing and separately dispensing a sunscreen and a UV indicator for use on the human skin, where the UV indicator is applied underneath the sunscreen on one or more small regions of the body, and is used to visually alert a user to apply more sunscreen or reduce their exposure to the sun.

Description of the Related Art

Sunscreens are widely used to reduce or prevent over exposure to ultraviolet (UV) radiation by reducing the level of UV radiation reaching the skin. Physical or inorganic sunscreens (such as those containing titanium dioxide or zinc oxide) generally operate by blocking or scattering UV radiation, whereas chemical or organic sunscreens generally operate by absorbing UV radiation.

A wide variety of sunscreen products are available. These sunscreens are typically commercially available as fluids, such as creams, lotions, gels and liquids, or as solids such as powders. Sunscreens are typically contained or packaged in flexible tubes or hard containers such as bottles, either plastic or metal, having dispensers such as orifices, nozzles, pumps, sprays or brushes. The packaging generally indicates the strength of UV protection afforded by the sunscreen (for example, a sun protection factor or SPF rating), and contains directions on proper application and reapplication procedures.

For a variety of reasons, once applied to the skin, sunscreens tend to become less effective over time. For example, the sunscreen may rub off, may be removed through sweating or immersion in water, and/or the effectiveness of the sunscreen may be reduced because of absorption into the skin or photo-degradation. Also, some sunscreens have a shelf-life and may become less effective upon prolonged storage. Generally the user cannot tell when a sunscreen is no longer providing effective or adequate UV protection. It can also be difficult for the user to know if they have applied an adequate coating of sunscreen to their skin in order to provide a desired degree of UV protection.

UV indicators that contain photochromic molecules, that reversibly change color upon exposure to UV radiation, are known. Formulations of such UV indicators that can be applied directly to human skin are presently being developed. Such UV indicators can be applied underneath a sunscreen as a marker on one or more small regions of the body, and used to visually alert a user to apply more sunscreen or reduce their exposure to the sun based on a change in color of the UV indicator marker. The color change that occurs when the sunscreen is no longer providing adequate UV protection can be, for example, from colored to colorless, colorless to colored, from one color to another, or can be a change in the intensity of the color, depending upon the particular UV indicator being used. UV indicators comprising molecules that change color irreversibly upon exposure to UV radiation are also known, and can be used as dosimeter-type indicators to give a visual indication of cumulative UV exposure.

BRIEF SUMMARY

Devices for containing and separately dispensing two materials for use on human skin are provided. In some embodiments, a device for containing and separately dispensing two materials for use on human skin has a primary chamber containing a sunscreen and a secondary chamber containing a UV indicator.

In some embodiments, a device for containing and separately dispensing two materials for use on human skin comprises a container and a double flip-top cap mounted thereto. The container defines a primary chamber for containing a primary material, and the double flip-top cap is mounted over an opening in the container. The double flip-top cap comprises a base via which it is mounted to the container and via which a primary material can be dispensed from the container. For example, the base can comprise a nozzle having an aperture. The double flip-top cap further comprises a middle section hinged to the base, the middle section serving as a flip-top lid for the container. The double flip-top cap further comprises a top section hinged to the middle section, the middle section and the top section cooperating to define a secondary chamber for containing a secondary material, and the top section serving as a flip-top lid for the secondary chamber. The primary and secondary materials have different compositions. In some embodiments, the primary material is a sunscreen and the secondary material is a UV indicator.

In some embodiments, a device for containing and separately dispensing two materials for use on human skin comprises a container and a dual cap assembly mounted thereto. The container defines a primary chamber for containing a primary material, and the dual cap assembly is mounted over an opening in the container. The dual cap assembly comprises a base via which it is mounted to the container and via which a primary material can be dispensed from the container. For example, the base can comprise a nozzle having an aperture. The dual cap assembly further comprises a middle section that can be removeably attached to the base to close off or provide access to the primary chamber, for example, by a snap-fit or screw thread fastening mechanism. The dual cap assembly further comprises a top section that can be removeably attached to the middle section to close off or provide access to a secondary chamber, for example, by a snap-fit or screw thread fastening mechanism. The middle section and top section cooperate to define the secondary chamber for containing a secondary material. The primary and secondary materials have different compositions. In some embodiments, the primary material is a sunscreen and the secondary material is a UV indicator.

In some embodiments of the devices described above, the container is a squeeze tube. In other embodiments of the devices described above, the container is a bottle. In some embodiments of the devices described above, the container is an aerosol can and the base comprises a spray nozzle.

In some embodiments of the devices described above, the secondary chamber contains an applicator for applying a UV indicator to human skin. The applicator can be a stamp (or die), for example.

Also provided are methods of using embodiments of the devices described herein to dispense and apply two materials to human skin.

In some embodiments, a method for dispensing two materials for application to human skin comprises: obtaining a device having a primary chamber containing a sunscreen and a secondary chamber containing a UV indicator. The method comprises opening the secondary chamber; dispensing and applying a quantity of the UV indicator from the secondary chamber to a first portion of the skin of a user; closing the secondary chamber; opening the primary chamber; dispensing a quantity of sunscreen from the primary container and applying it over the UV indicator on the first portion of the skin of the user and to a second portion of the skin of the user; and closing the primary chamber.

In other embodiments, a method for dispensing two materials for application to human skin comprises: obtaining a device having a container defining a primary chamber containing sunscreen and a double flip-top cap mounted to the container, the double flip-top cap comprising a secondary chamber containing a UV indicator; flipping open a hinged top section of the double flip-top cap to provide access to the secondary chamber, for example by partially disengaging the top section from a middle section of the double flip-top cap; dispensing and applying a quantity of the UV indicator from the secondary chamber to a first portion of the skin of a user, for example, using a stamp located in the secondary chamber; closing the top section of the double flip-top cap, for example, by re-engaging the hinged top section with the middle section; flipping open a hinged middle section of the double flip-top cap to provide access to the primary chamber, for example, by partially disengaging the middle section from a base of the double flip-top cap; dispensing a quantity of sunscreen from the primary chamber via the base and applying it over the UV indicator on the first portion of the skin of the user and to a second portion of the skin of the user; closing the middle section of the double flip-top cap, for example, by re-engaging the hinged middle section with the base.

In still further embodiments, a method for dispensing two materials for application to human skin comprises: obtaining a device comprising a container defining a primary chamber containing sunscreen and a dual cap assembly mounted to the container, and the dual cap assembly comprising a secondary chamber containing a UV indicator; separating a top section of the dual cap assembly from a middle section of the dual cap assembly to provide access to the secondary chamber; dispensing and applying a quantity of the UV indicator from the secondary chamber to a first portion of the skin of a user, for example, using a stamp located in the secondary chamber; re-attaching the top section of the dual cap assembly to the middle section of the dual cap assembly to close off the secondary chamber; separating the middle section of the dual cap assembly from a base of the dual cap assembly to provide access to the primary chamber; dispensing a quantity of sunscreen from the primary chamber via the base and applying it over the UV indicator on the first portion of the skin of the user and to a second portion of the skin of the user; re-attaching the middle section of the dual cap assembly to the base dual cap assembly to close off the primary chamber.

These and other features, and advantages of the present invention will become more readily apparent from the attached drawings and the detailed description of preferred embodiments, which follow.

BRIEF DESCRIPTION OF THE DRAWINGS

FIG. 1 is a side view of an embodiment of a device for containing and separately dispensing materials for use on human skin, the device comprising a primary chamber and a double flip-top cap comprising a secondary chamber;

FIGS. 2A, 2B, 2C, and 2D are various different views of the double flip-top cap shown in FIG. 1;

FIGS. 5A, 5B, 5C and 5D are side views of the double flip-top cap shown in FIG. 1 with the hinged sections in different positions;

FIG. 8 is a side view of another embodiment of a device for containing and separately dispensing materials for use on human skin, the device comprising a spray can and a cap assembly comprising a spray nozzle and a secondary chamber;

Like reference numerals refer to like parts throughout the several views of the drawings.

DETAILED DESCRIPTION OF PREFERRED EMBODIMENTS

Figure 3A:
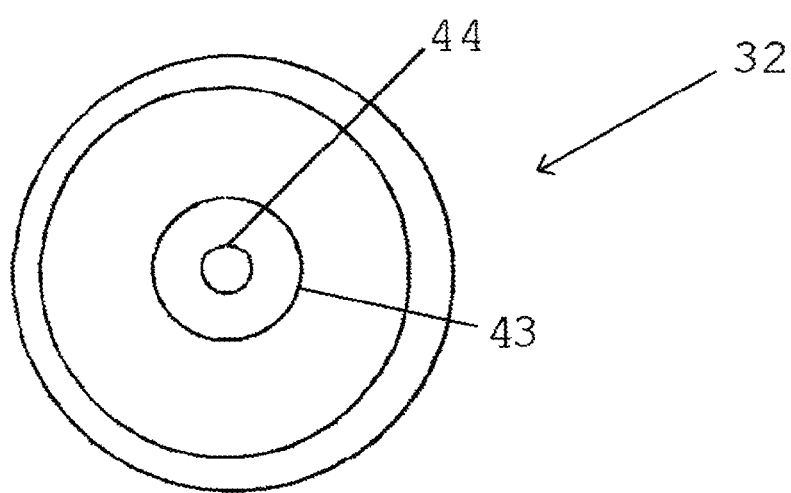
FIGS. 3A and 3B are top and side cutaway views of the base of the double flip-top cap shown in FIG. 1.

As used herein, the term "sunscreen" includes materials sold for use on human skin to reduce exposure of the skin to UV radiation and protect exposed skin from sunburn, for example, by absorbing, scattering and/or blocking UV radiation. Sunscreens include fluids such as creams, lotions, liquids, gels, sprays and balms, and include solids such as powders.

As used herein, the term UV indicator refers to materials comprising one or more types of photochromic molecules that change color when exposed to UV radiation. The color change is preferably reversible, but in some embodiments is irreversible. UV indicators can include fluids such as solutions, suspensions, inks or gels comprising photochromic molecules, or solids such as powders comprising photochromic molecules.

Figure 1:
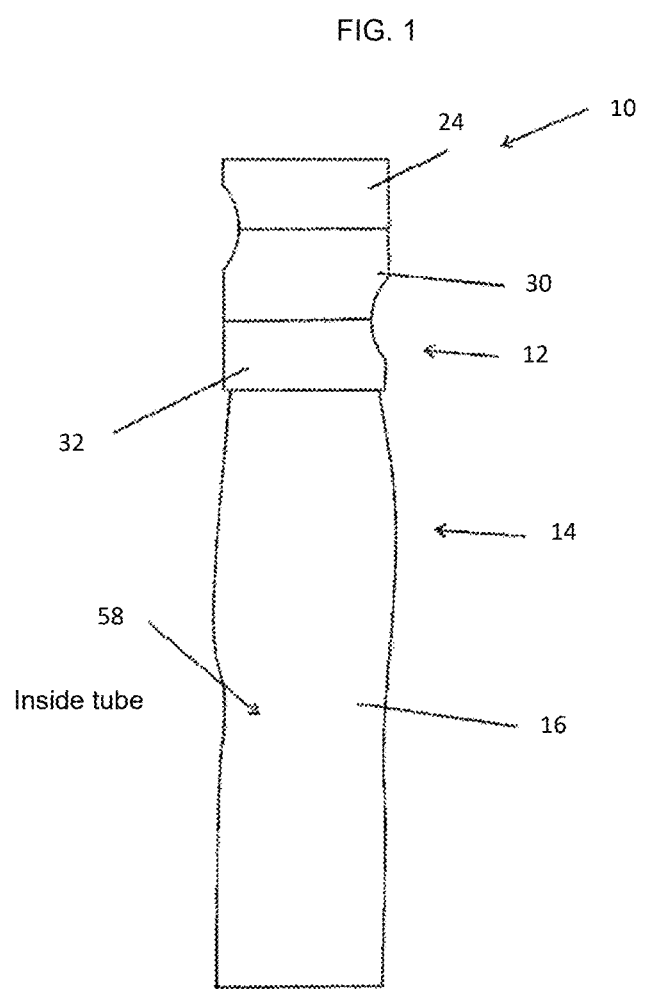

Referring to FIG. 1, an embodiment of a device 10 for containing and separately dispensing two materials for use on human skin is shown. Device 10 comprises a container 14, and a double flip-top cap 12 mounted on container 14. Although container 14, is illustrated in FIG. 1 as a flexible squeeze tube it can be, for example, a hard-walled container such as a bottle or can. In different embodiments, walls 16 of primary container 14 can be made of flexible or rigid plastic, flexible or rigid metal, glass, composite materials or other suitable materials. Walls 16 define a primary chamber (i.e., an interior volume of container 14) containing a primary material, such as a sunscreen 58.

Double flip-top cap 12 comprises a base 32 via which it is mounted to container 14 and via which sunscreen 58 is dispensed. A middle section 30 of cap 12 is hinged to base 32 and serves as a flip-top lid or closure for container 14 for closing off and providing access to the primary chamber. A top section 24 of cap 12 is hinged to middle section 30. Middle section 30 and top section 24 cooperate to define a secondary chamber containing an indicator (as shown in further detail in reference to FIGS. 4 and 5 below). Top section 24 serves as a flip-top lid or closure for closing off and providing access to the secondary chamber. The secondary chamber can contain a secondary material, such as a UV indicator.

A primary material, such as sunscreen 58 can be dispensed from within container 14 via base 32 when middle section 30, serving as a flip-top lid, is opened. When middle section is in a closed position, as shown in FIG. 1, primary chamber in container 14 is closed off or substantially sealed. A secondary material, such as a UV indicator, can be dispensed from the secondary chamber when top section 24, serving as a flip-top lid, is opened. When top section 24 is in a closed position, as shown in FIG. 1, the secondary chamber is closed off or substantially sealed. Base 32 is typically mounted to container 14 connected by a screw thread fastening mechanism (see FIGS. 6 and 7).

FIGS. 2A, 2B, 2C and 2D are right-side, left-side, front and top views, respectively, of the double flip-top cap 12 shown in FIG. 1. Flexible hinges 34 and 36 attach top section 24 to middle section 30, and middle section 30 to base 32, respectively. Hinges 34 and 36 are preferably on opposite sides of the double flip-top cap 12 as shown in FIGS. 2A and 2B, so that when one section (30 or 24) is flipped to an open position, the other section has less tendency to open at the same time. In other embodiments the flexible hinges 34, 36 could be on the same side of the cap or at some other position relative to one another. The double flip-top cap 12 is typically made of plastic, and flexible hinges 34 and 36 can be made of thin plastic integrally formed with the rest of the cap, as is conventional and is well known to those skilled in the art. In some embodiments, the top section 24 and the middle section 30 can be formed together, the base 32 formed separately and these two parts connected via, for example, a slip-fit connection to form hinge 34. In some embodiments, the base 32 and the middle section 30 can be formed together, the top section 24 formed separately and these two parts connected via, for example, a slip-fit connection forming hinge 36. Indents 38 and 40 shown in FIG. 2C provide an area upon which fingers can grip to open the flip-top lids (sections 24 and 30 respectively).

Figure 3B:
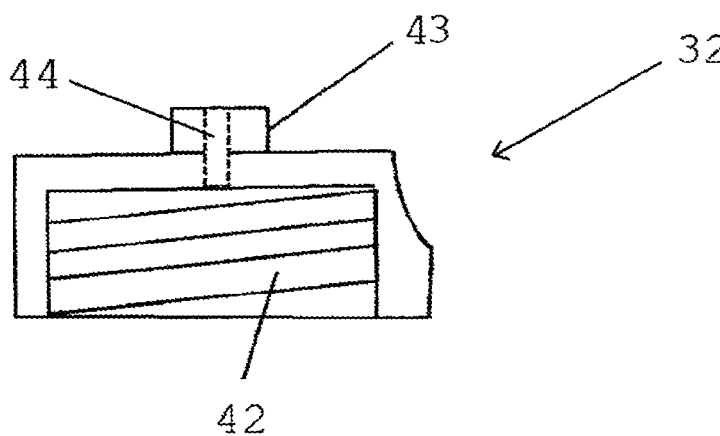

FIGS. 3A and 3B illustrate a top view and a side cutaway view, respectively, of base 32 of double flip-top cap 12. Base 32 comprises a protruding nozzle 43, with opening or aperture 44 formed therethrough, via which the primary material such as sunscreen 58 can be dispensed from a container to which base 32 is mounted. As shown in FIG. 3B, base 32 is internally threaded with threads 42 via which it can be mounted to an externally threaded container.

Figures 4A, 4B, 4C:
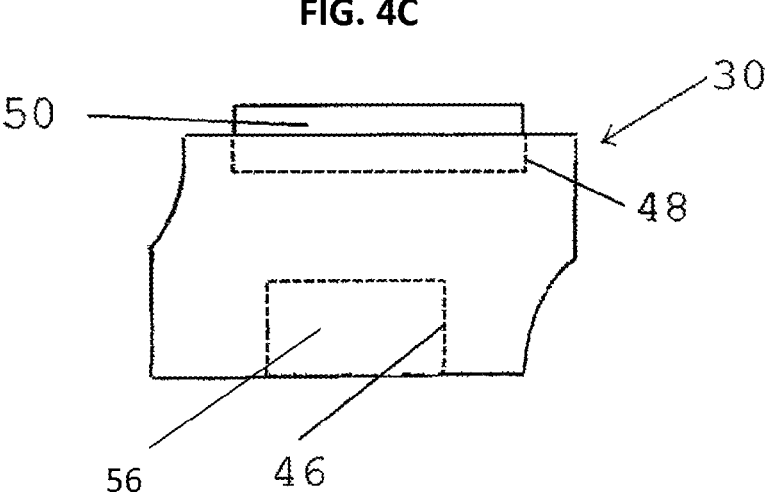
FIGS. 4A, 4B and 4C are underside, top and side views of the middle section of the double flip-top cap shown in FIG. 1, and FIGS. 4D, 4E and 4F are top, underside, and side views of the top section of the double flip-top cap shown in FIG. 1.
Figure 11:
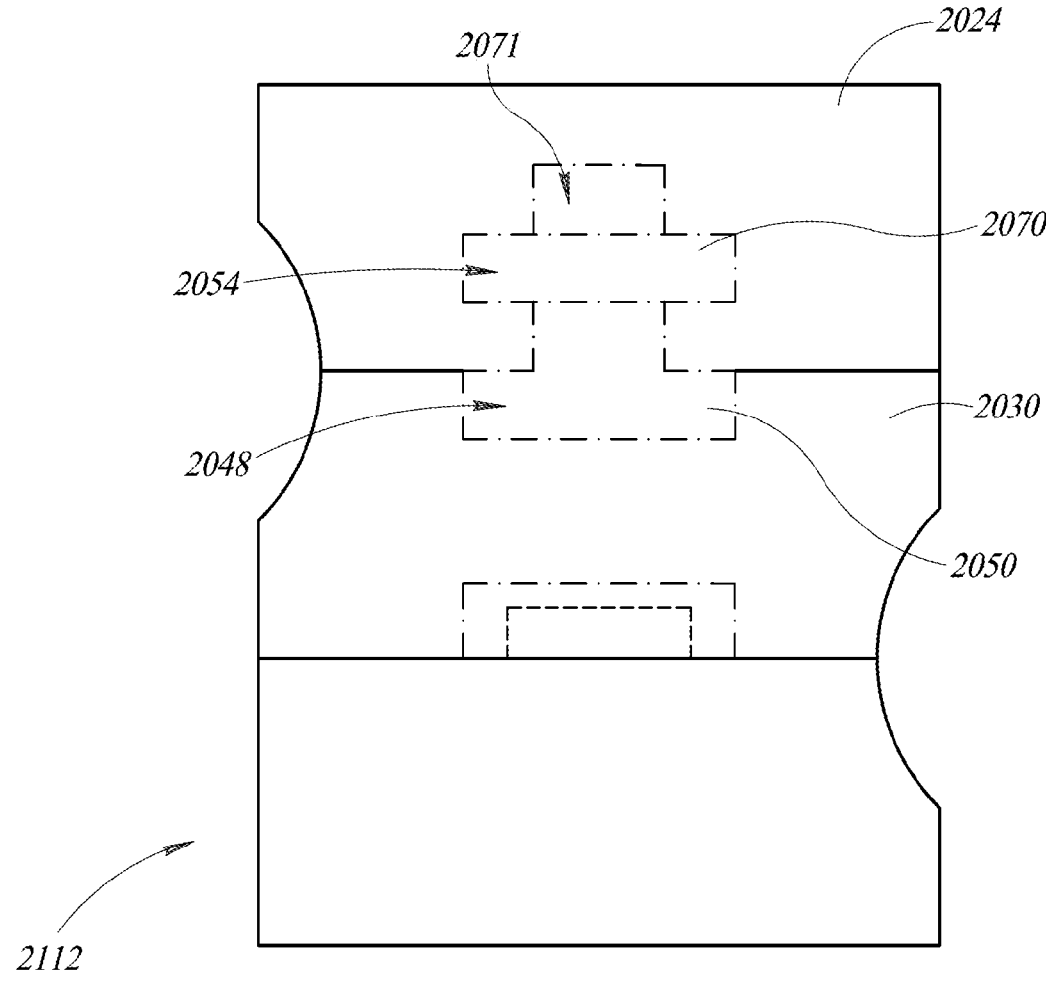
FIG. 11 is a side view of a double flip-top cap according to another embodiment.

FIGS. 4A-C show an underside view, a top view and a side view, respectively, of the middle section 30 of double flip-top cap 12. Middle section 30 has a recess 46 formed therein that fits over protruding nozzle 43 of base 32, to prevent leakage of material via aperture 44, when middle section 30 is in a closed position with respect to base 32. In other embodiments, middle section 30 may comprise a plug that inserts into aperture 44 to block it when middle section is in a closed position. Other suitable sealing mechanisms that will be apparent to those skilled in the art may be incorporated into middle section 30 and/or base 32 for this purpose. Middle section 30 also comprises another recess 48 containing a stamp 50 that may be impregnated or soaked with the secondary material, such as a UV indicator ink. The stamp can be made of a polymer foam or a sponge-like rubber or other suitable material. It may be patterned with an image or design such as image 52. FIGS. 4D-F show a top view, an underside view and a side view, respectively, of the top section 24 of double flip-top cap 12. Top section 24 has a recess 54 to that fits over and accommodates stamp 50 that protrudes from recess 48 in middle section 30. Thus, top section 24 and middle section 30 cooperate to define a secondary chamber 56, formed by recesses 54 and 48, for containing a secondary material, which in the illustrated embodiment is a UV indicator ink stored in stamp 50. In the illustrated embodiment, recesses 48 and 54 have approximately the same dimensions. In some embodiments there is a patterned stamp located in one recess (for example recess 48) and an ink pad located impregnated with a UV indicator ink located in the other recess (for example, recess 54). When top section 24 is in a closed position the stamp is in contact with the pad to wet or load the stamp with ink. In some embodiments, an ink well can be provided to be in fluid communication with an ink pad, which ink pad can wet or load the stamp with ink as illustrated in FIG. 11 and described in more detail below.

In some embodiments the stamp and/or ink pad are readily removable so that they can be replaced or refilled. In some embodiments recesses 48 and 54 are different sizes or depths, and in some embodiments there is a recess in only one of the top section 24 or middle section 30.

A gasket or other suitable sealing mechanism (not shown) can be used to substantially seal secondary chamber 56 when top section 24 is in a closed position with respect to middle section 30, so that secondary material (such as a UV indicator) does not leak from secondary chamber 56, and so that there is less tendency for stamp 50 and/or an ink pad (if present) in the secondary chamber to dry out.

FIGS. 5A, 5B, 5C, and 5D illustrate views of double flip-top cap 12 with the hinged sections in different positions. In FIG. 5A middle section 30 is engaged with base 32 and top section 24 is engaged with middle section 30, so both flip-top lids (sections 30 and 24) are in a closed position. A snap-fit mechanism or other suitable mechanism can be used so that a reasonable degree of manual force is required to open the lids, so that there is less tendency for them to open accidently when device 10 is not in use. In FIG. 5B middle section 30 is pivoted to an open position. In FIG. 5C top section 24 is flipped or pivoted to an open position. In FIG. 5D both middle section 30 and top section 24 are flipped or pivoted to an open position. Nozzle 44 and recesses 46, 48 and 54 are shown with dotted lines in FIGS. 5A and 5C.

A method of use of device 10 having double flip-top cap 12 such as shown in FIGS. 1-5 is as follows: hinged top section 24 is flipped open and the exposed stamp 50 having the UV indicator material therein is used to apply a quantity of UV indicator to a small region of the skin in areas of high exposure such as the arms, shoulders, or back. Hinged top section 24 is closed and then hinged middle section 30 is opened by flipping it in the opposite direction from how top section 24 was opened. Sunscreen is dispensed from the primary chamber in container 14; the sunscreen material is applied over the UV indicator that was applied to a small region of the skin and to other portions of the user's sun-exposed skin as desired. The UV indicator may be applied as any suitable mark or shape such as a round spot or in a predetermined design such as a flower, animal, etc.

The applied UV indicator will change color based upon the intensity and length of exposure to UV radiation through the sunscreen. The device may include directions as to the significance of different colors or levels of color saturation. A bright red spot, for example, may provide a warning that additional sunscreen should be applied.

Figure 6:
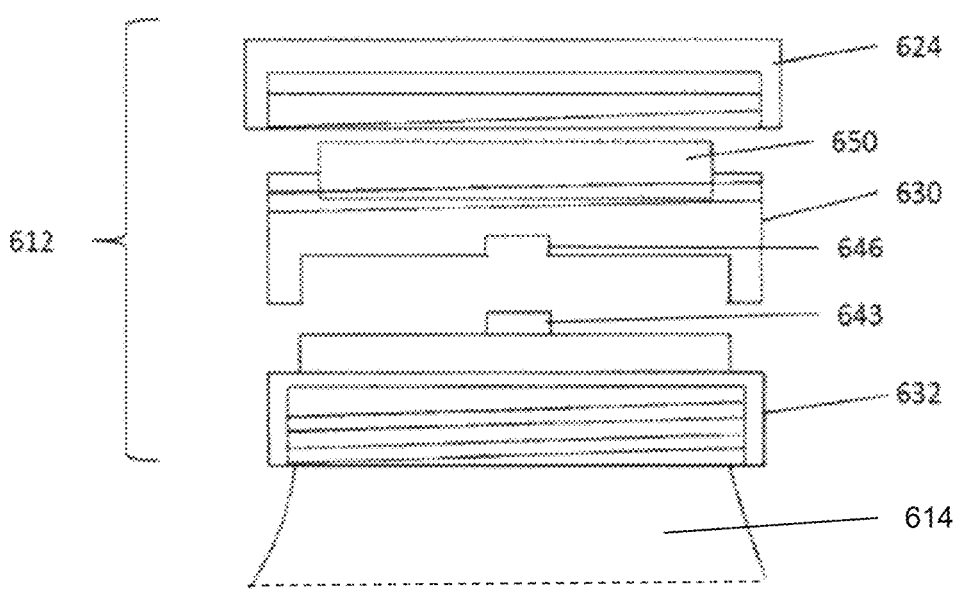
FIG. 6 is a cross-sectional side view of an embodiment of a dual cap assembly mounted on a container.
Figure 7:
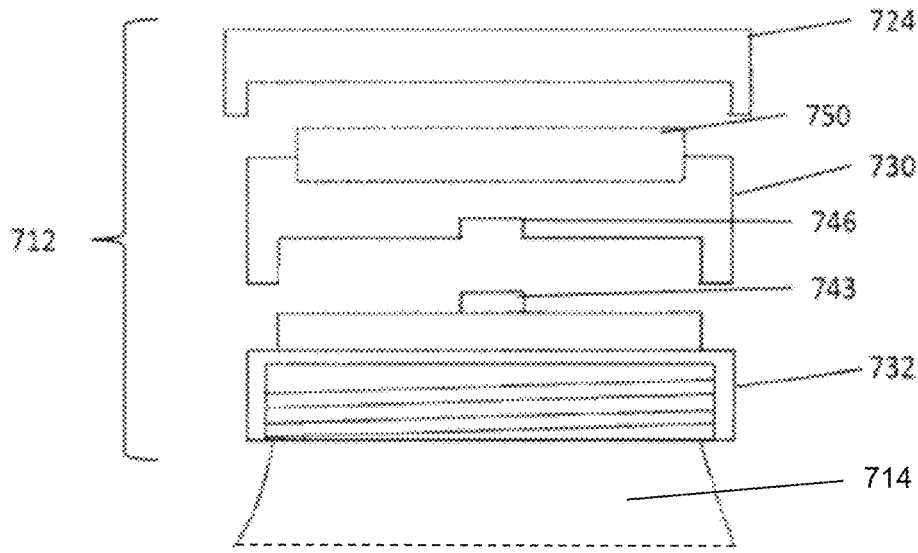
FIG. 7 is a cross-sectional side view of another embodiment of a dual cap assembly mounted on a container.

The double flip-top cap as shown above has two hinged sections. Other suitable mechanisms may be used for removeably attaching or fastening various sections of a cap assembly to one another. The cap can comprise snap-fit, push-on or screw-on sections or a combination of attachment mechanisms. For example, in some embodiments one or both hinges 34 and 36 are omitted, and middle section 30 removeably snap-fits to base 32 and/or top section 24 removeably snap-fits to middle section 30 (such as shown in FIG. 7 below). In other embodiments (such as shown in FIG. 6 below) middle section 30 is removeably fastened to base 32 and/or top section 24 is removeably fastened to middle section 30 by a screw thread fastening mechanism. In general the hinges are more convenient for ease of use of the device, and for keeping the components of the device together.

Thus, double flip-top cap 12 illustrated in FIGS. 1-5 can allow a single device to be used to store and dispense two materials for application to human skin, that are to be used in association with one another. The double flip-top cap 12 is a convenient way of sealing and providing access to a primary chamber in container 14 to which the cap is mounted, and to a secondary chamber within the cap 12 itself. The double flip-top cap thereby facilitates storage and separate dispensing of a primary material and a secondary material for use on human skin, and in particular storage and separate dispensing of a sunscreen and a UV indicator. The indicator can be applied to the skin using a stamp or other suitable applicator that is contained within the secondary chamber.

Some alternative embodiments of devices for storing and separately dispensing a sunscreen and a UV indicator are illustrated in FIGS. 6-11.

In the embodiment shown in FIG. 6 a dual cap assembly 612 is mounted to a container 614 (only partially shown in FIG. 6). Dual cap assembly comprises base 632 which is mounted to container 614 by a screw thread fastening mechanism. Base 632 has a nozzle 643 (with an aperture therethrough) for dispensing sunscreen from container 614. Middle section 630 removeably snap-fits on to base 632, with recess 646 accommodating nozzle 643 to close off container 614 and preferably form a seal over the aperture in nozzle 643. Top section 624 removeably screws on to middle section 630 by a screw thread fastening mechanism. Sections 624 and 630 define a secondary chamber holding an inked stamp 650 and optionally an ink pad (not shown).

In the embodiment shown in FIG. 7 a dual cap assembly 712 is mounted to a container 714 (only partially shown in FIG. 7). Dual cap assembly comprises base 732 which is mounted to container 714 by a screw thread fastening mechanism. Base 732 has a nozzle 743 (with an aperture therethrough) for dispensing sunscreen from container 714. Middle section 730 removeably snap-fits on to base 732, with recess 746 accommodating nozzle 743 to close off container 714 and preferably form a seal over the aperture in nozzle 743. Top section 724 snap-fits on to middle section 730. Sections 724 and 730 define a secondary chamber holding an inked stamp 750 and optionally an ink pad (not shown).

Figure 8:
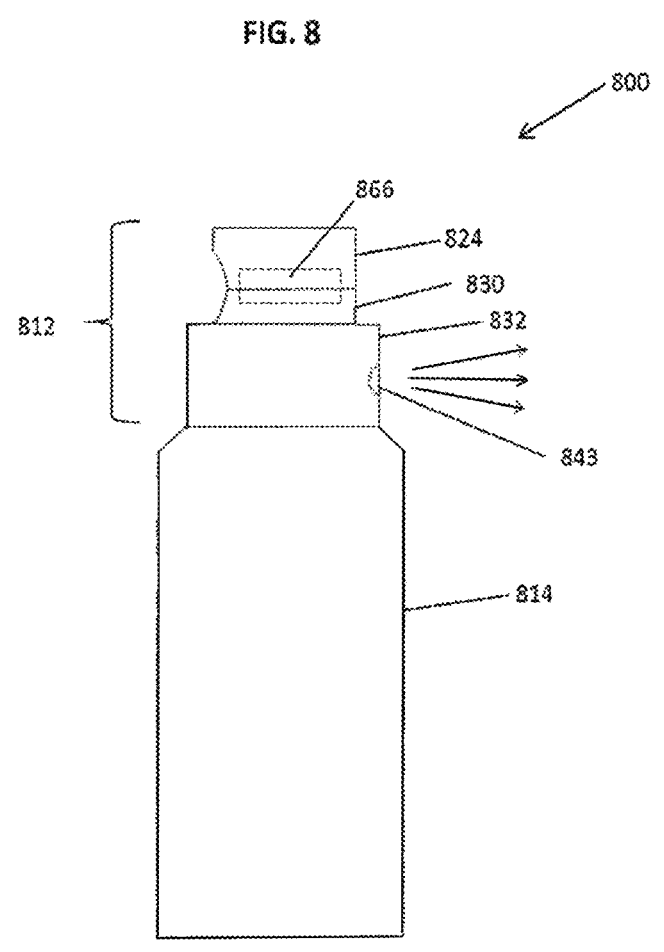

FIG. 8 shows a device 800 for containing and separately dispensing two materials for use on human skin, the device 800 comprising an aerosol or pump-spray container 814 having a dual cap assembly 812 mounted thereon. Sunscreen is dispensed from container 814 via a nozzle 843 in base 832 by pressing down on dual cap assembly 812. Dual cap assembly 812 further comprises a middle section 830 and top section 824. Top section can be a flip-top lid, a screw-on lid, a snap-fit lid or the like as described above. Middle section 830 and top section 824 define a secondary chamber 866 containing a UV indicator for use with the sunscreen in container 814. Middle section can be integrally formed with base 832, or can be fixed to base 832 or can be removeable attached to base 832.

Figure 9:
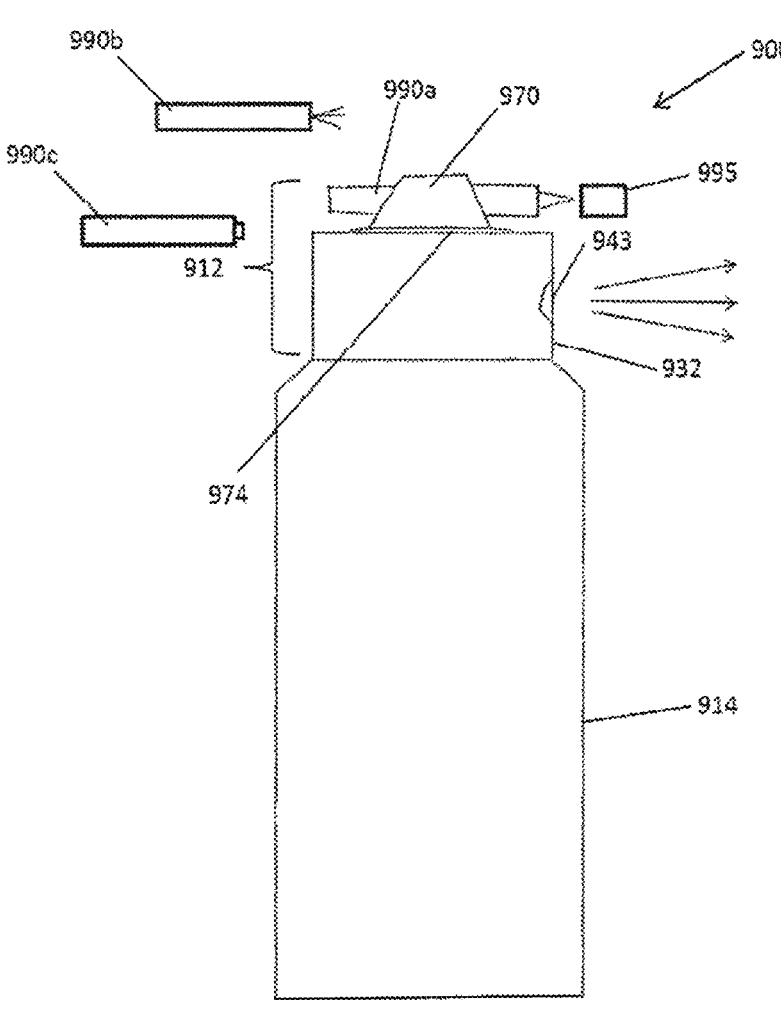
FIG. 9 is a side view of another embodiment of a device for containing and separately dispensing materials for use on human skin, the device comprising a spray can and cap assembly with a container/applicator detachably mounted thereto.

FIG. 9 shows a device 900 for containing and separately dispensing two materials for use on human skin, the device 900 comprising an aerosol or pump-spray container 914 having a cap assembly 912 mounted thereon. Sunscreen is dispensed from container 914 via a nozzle 943 in base 932 by pressing down on cap assembly 912. Cap assembly 912 further comprises a flexible clip 970 via which a container/applicator device such as pen 990a, brush 990b or stamp 990c can be removeably mounted to base 932. Container/applicator device 990 contains a UV indicator which can be applied to human skin using the device, for use in association with sunscreen stored in container 914. A removable cap 995 is used to close off or seal container/applicator device when not in use. Flexible clip 970 can be integrally formed with base 932 or can be fastened to base 932 using an adhesive or glue 974 as shown in FIG. 9.

Figure 10:
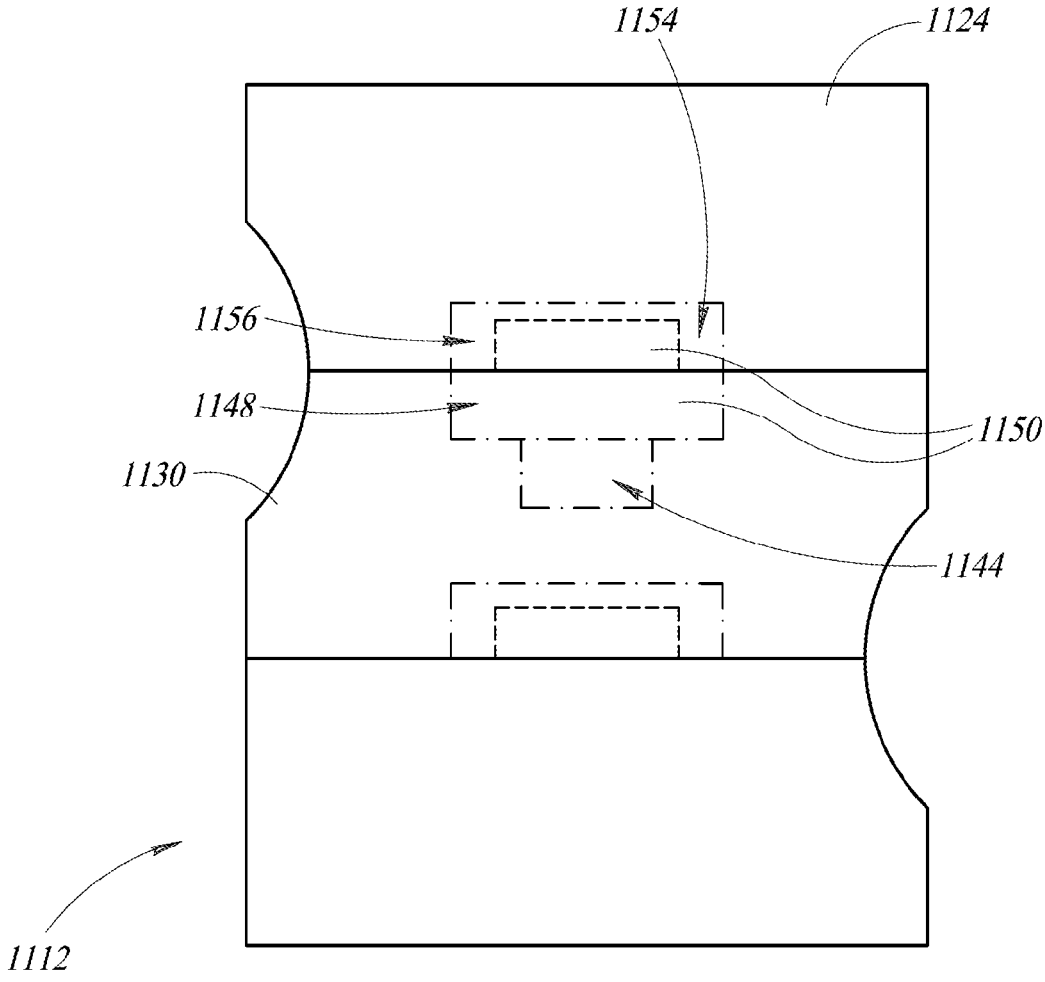
FIG. 10 is a side view of a double flip-top cap according to another embodiment.

FIG. 10 shows a side view of a double flip-top cap 1112 according to another example embodiment. The double flip-top cap 1112 can be mounted to a wide variety of containers, for example, containers 14, 614, 714, 814, etc., which have not been shown for clarity of illustration and description. The double flip-top cap 1112 is generally similar to the double flip-top cap 12, but provides a variation in which the double flip-top cap 1112 includes an ink well recess 1144 that partially extends through a middle section 1130. In particular, the ink well recess 1144 is located below a recess 1148 that extends through the middle section 1130 from an upper surface of the middle section 1130. The ink well recess 1144 is sized and shaped to receive UV indicator ink. In this manner, a secondary chamber 1156 is defined at least in part by a recess 1154 disposed in a top section 1124, the recess 1148 and the ink well recess 1144 disposed in the middle section 1130.

In this embodiment of the double flip-top cap 1112, a self-inking UV applicator 1150, e.g., a foam stamp, is positioned in the recess 1148 of the middle section 1130, with an upper portion protruding outwardly from the recess 1148 of the middle section 1130 and into the recess 1154 of the top section 1124. A lower side of the self-inking UV applicator 1150 is positioned adjacent to the ink well recess 1144 and is in fluid communication with the ink well recess 1144. Providing an ink well recess 1144 in fluid communication with the UV applicator 1150 allows the UV applicator 1150 to become re-saturated between uses and provides a metered volume of ink. The metered volume of ink material generally results in a relatively consistent thickness of the ink layer deposited on the skin of the user, which positively contributes to a perceived depth of color change when the UV indicator ink, e.g., photochromic dye, is exposed to UV radiation. For example, the protrusion of the UV applicator 1150 above a rim of the middle section 1130 can result, upon re-saturation of the UV applicator 1150 and a standardized compression of the UV applicator 1150, in deposition of approximately similar amounts of ink.

Moreover, the positioning of the self-inking UV applicator 1150 adjacent to the ink well recess 1144 and in fluid communication with the UV indicator ink disposed therein allows for re-saturation of the self-inking UV applicator 1150. For instance, the ink well recess 1144 and the self-inking UV applicator are sized and shaped to allow capillary forces to pull or draw the UV indicator ink disposed in the ink well recess 1144 toward the self-inking UV applicator 1150 to re-saturate the UV applicator 1150. In some instances, the re-saturation of the UV applicator 1150 via capillary forces can work in tandem with gravitational forces. For instance, when a device having the double flip-top cap 1112 coupled to a container is positioned with an exterior surface of the top section 1124 facing or abutting a horizontal or an inclined surface, the gravitational forces along with the capillary forces can direct or draw the UV indicator ink toward the UV applicator 1150 and re-saturate the UV applicator 1150. In some instances, when the device is positioned on a horizontal or an inclined surface such that a right side or a left side of the device is facing or abutting the horizontal or the inclined surface, the gravitational forces along with the capillary forces can direct or draw the UV indicator ink toward the UV applicator 1150 and re-saturate the UV applicator 1150. Again, providing the ink well recess 1144 and positioning the ink well recess 1144 adjacent to the UV applicator 1150 in this manner advantageously allows for re-saturation of the UV applicator 1150 which, in conjunction with the UV applicator 1150 extending above the rim of the middle section 1130 and compressed a standardized amount when pressed against the user's skin (contact with the upper rim of middle section 1130 with the user's skin determining the amount of compression), allows for a relatively consistent metering of the ink layer deposited on the skin of the user between uses and through the lifecycle of the device.

Moreover, the self-inking UV applicator 1150 described above can be provided in a wide variety of devices. For example, the container 614 illustrated in FIG. 6 can include an ink well recess disposed in the middle section 630 with UV indicator ink disposed in the ink well recess to pull or draw the UV indicator ink to re-saturate the UV applicator 1150. Similarly, the middle sections 730, 830 of corresponding dual cap assembly 712 and device 800 can also include an ink well recess to pull or draw the UV indicator ink to re-saturate the UV application 1150.

FIG. 11 illustrates a double flip-top cap 2112 according to another example embodiment. The double flip-top cap 2112 provides a variation in which it includes a stamp 2050 located in one recess (for example recess 2048 of a middle section 2030) and an ink pad 2070 impregnated with a UV indicator ink located in another other recess (for example, recess 2054 of a top section 2024). The double flip-top cap 2112 also includes an ink well 2071 located in the top section 2024 that includes UV indicator ink and is in fluid communication with the ink pad 2070. When top section 2024 is in a closed position, the stamp 2050 is in contact with the ink pad 2070 to wet or load the stamp 2050 with ink. The UV indicator ink in the ink well 2071 can saturate or re-saturate the ink pad 2070.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

The various implementations, examples, and embodiments described above can be combined to provide further implementations, examples, and embodiments respectively. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet are incorporated herein by reference, including but not limited to U.S. Provisional Patent Application Ser. No. 62/338,235 filed May 18, 2016.

What is claimed is:

1. A device for containing and separately dispensing two materials for use on human skin, the device comprising:
   a container defining a primary chamber for containing a primary material, said container comprising an opening; and
   a double flip-top cap mounted to said container over said opening, said double flip-top cap comprising:
      a base via which said double flip-top cap is mounted to said container and via which said primary material is dispensed from said container;
      a middle section hinged to said base, said middle section serving as a first flip-top lid for said container and defining a middle section recess including an upper rim, the middle section recess containing a secondary material and in fluid communication with a stamp, wherein the stamp is impregnated or soaked with the secondary material, and wherein an upper portion of the stamp protrudes outwardly from the upper rim of the middle section recess exposing a defined extent of the stamp providing a metered quantity of the secondary material when the stamp is pressed onto the skin, pressure applied by the stamp on the skin being limited by contacting the skin with the upper rim of the middle section; and
      a top section hinged to said middle section, said top section defining a recess that fits over and accommodates the stamp, and said top section serving as a second flip-top lid for said stamp.

2. The device of claim 1 wherein said base comprises a nozzle having an aperture via which said primary material is dispensed from said primary chamber.

3. The device of claim 1 wherein said container is a flexible tube or a bottle.

4. The device of claim 1 wherein said container is made of plastic or metal, and said double flip-top cap is made of plastic.

5. The device of claim 1 wherein said middle section is hinged to said base by a first flexible hinge and said top section is hinged to said middle section by a second flexible hinge, said first and second flexible hinges being located on circumferentially opposite sides of said middle section so as to substantially prevent opening of said first and second flip-top lids simultaneously.

6. A device for containing and separately dispensing two materials for use together on human skin comprising:
   a container defining a primary chamber for containing a sunscreen, said container comprising an opening; and
   a dual cap assembly mounted to said container over said opening, said dual cap assembly comprising:
      a base via which said dual cap assembly is mounted to said container and via which said sunscreen is dispensed from said container;
      a middle section removably attached to said base to close off and provide access to said primary chamber, said middle section defining a middle section recess containing a UV indicator ink in fluid communication with a stamp, wherein the stamp is impregnated or soaked with the UV indicator ink, and wherein an upper portion of the stamp protrudes outwardly from the middle section recess exposing a defined extent of the stamp providing a metered quantity of the UV indicator ink when the stamp is pressed onto the skin, pressure applied by the stamp on the skin being limited by contacting the skin with the upper rim of the middle section; and a top section removably attached to said middle section to close off or provide access to the stamp, the top section defining a recess that fits over and accommodates the stamp.

7. The device of claim 6 wherein said middle section is removably attached to said base by a snap-fit or screw thread fastening mechanism, and said top section is removably attached to said middle section by a snap-fit or screw thread fastening mechanism.

8. The device of claim 6 wherein said base comprises a nozzle having an aperture via which said sunscreen is dispensed from said primary chamber.

9. The device of claim 6 wherein said container is a flexible tube or a bottle.

10. The device of claims 6 wherein said container is made of plastic or metal, and said dual cap assembly is made of plastic.

11. A method of dispensing two materials for application to human skin using a device as claimed in claim 1, said method comprising:

flipping open said hinged top section of said double flip-top cap to provide access to said stamp;

dispensing and applying a quantity of said secondary material from said stamp to a first portion of the skin of a user;

closing said hinged top section of said double flip-top cap;

flipping open said hinged middle section of said double flip-top cap to provide access to said primary chamber;

dispensing a quantity of primary material from said primary chamber via said base and applying it over said secondary material applied to said first portion of skin and to a second portion of the skin of said user; and closing said hinged middle section of said double flip-top cap.

12. A method of dispensing two materials for application to human skin using a device as claimed in claim 6, said method comprising:

separating said top section of said dual cap assembly from said middle section to provide access to said stamp;

dispensing and applying a quantity of said UV indicator ink from said stamp to a first portion of the skin of a user;

re-attaching said top section of said dual cap assembly to close off access to said stamp;

separating said middle section of said dual cap assembly from said base to provide access to said primary chamber;

dispensing a quantity of sunscreen from said primary chamber via said base and applying it over said UV indicator ink applied to said first portion of skin and to a second portion of the skin of said user; and re-attaching said middle section of said dual cap assembly to said base to close off said primary chamber.

13. The device of claim 1 wherein said primary material is a sunscreen and said secondary material is a UV indicator ink.

\* \* \* \* \*